United States Patent [19]

Babb et al.

[11] Patent Number: 4,803,161

[45] Date of Patent: Feb. 7, 1989

[54] BIOLOGICAL AND ANALYTICAL USES OF PHENALENONE AND BENZPHENALENONE COMPOUNDS

[75] Inventors: Bruce E. Babb, Rochester; Robert T. Belly, Webster; Albert J. Mura, Rochester, all of N.Y.

[73] Assignee: Eastman Kodak Company, Rochester, N.Y.

[21] Appl. No.: 824,757

[22] Filed: Jan. 31, 1986

[51] Int. Cl.$^4$ .............................................. C12Q 1/02
[52] U.S. Cl. .......................................... 435/29; 435/4; 436/546; 436/800; 436/805; 564/426; 564/427; 568/63; 568/326
[58] Field of Search ............ 435/4, 29; 436/800; 564/427, 426; 568/326, 63

[56] References Cited

U.S. PATENT DOCUMENTS 4,144,306  3/1979  Figueras ............................... 422/56
4,307,188  12/1981 White ..................................... 435/4

OTHER PUBLICATIONS

Kuznetsova et al.–Chem. Abst., vol. 96, (1982), p. 217,019e.
Solodar et al.—Chem. Abst., vol. 94 (1981), p. 3873p.
Solodar et al.—Chem. Abst., vol. 93 (1980), p. 168,007b.
Wolfbeis et al., Bull. Chem. Soc. Japan, 58, pp. 731–734 (1985).
Koller et al., Anal. Biochem. 143, pp. 146–151 (1984).
Cooke et al., Austral. J. Chem. 11, pp. 230–235 (1958).
Solodar et al., Zhurnal Organicheskoi Khinii, 16, (5), pp. 1062–1064 (1980).

Primary Examiner—Sam Rosen
Attorney, Agent, or Firm—J. Lanny Tucker

[57] ABSTRACT

Certain phenalenone and benzphenalenone fluorescent compounds are useful in biomedical studies and analytical determinations. These compounds are particularly useful in assays for living organisms, e.g. microorganisms, carried out at a pH of 9 or less. For these determinations, the compounds can be attached to reducible compounds which will subsequently release the fluorescent moiety upon reduction. In the presence of an electron transfer agent, the reducible compounds are easily reduced by a microorganism.

22 Claims, 1 Drawing Sheet

BIOLOGICAL AND ANALYTICAL USES OF PHENALENONE AND BENZPHENALENONE COMPOUNDS

CROSS-REFERENCE TO RELATED APPLICATIONS

Reference is made to the following copending and commonly assigned applications:

U.S. Ser. No. 824,766, filed on even date herewith by Belly et al and entitled REDUCIBLE COMPOUNDS AND ANALYTICAL COMPOSITIONS, ELEMENTS AND METHODS UTILIZING SAME which is a continuation-in-part of U.S. Ser. No. 699,386, filed Feb. 7, 1985, U.S. Ser. No. 824,756, filed on even date herewith by Babb et al and entitled HYDROLYZABLE FLUORESCENT SUBSTRATES AND ANALYTICAL DETERMINATIONS USING SAME, and U.S. Ser. No. 825,755, filed on even date herewith by A. Wu and entitled USE OF POLYMERIC MORDANTS TO INCREASE THE INTENSITY OF RIGID FLUORESCENT DYES.

FIELD OF THE INVENTION

This invention relates to the use of phenalenone and benzphenalenone compounds in biomedical studies and clinical chemistry. In particular, it relates to analytical compositions and elements useful in analytical methods for the determination of various analytes, including biological species, e.g. microorganisms, in aqueous liquids, e.g. biological fluids. It also relates to certain novel benzphenalenone compounds.

BACKGROUND OF THE INVENTION

The staining of biological tissues and cells with dyes, especially fluorescent dyes, in order to differentiate one type from another or to render them more observable, is well known in the art. Dyes that fluoresce in the red region of the electromagnetic spectrum are especially desirable.

Further, chemical analysis of liquids, such as water, milk and biological fluids is often desirable or necessary for health maintenance and diagnostic care. Various compositions and elements to facilitate such analyses are known. Such compositions and elements generally include a reagent composition for determining a substance under analysis, identified as an "analyte" herein. The analyte can be a living organism, such as a microorganism or yeast cell, or a nonliving chemical substance. The reagent composition, upon interaction with the analyte, provides a detectable change (e.g. dye formation).

Recently, much work has been directed to developing compositions and elements which are useful for rapid and highly quantitative diagnostic or clinical analysis of biological fluids such as whole blood, blood sera, plasma, urine and the like.

For example, for the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. Most urinary tract infections are associated with bacterial counts of 100,000 or more organisms per ml of urine, a condition referred to as significant bacteriuria In the Belly et al patent application noted above, i.e. U.S. Ser. No. 824,766, novel reducible compounds are described and claimed which are useful in the detection of bacteria as well as other oxidizable analytes. The assays described in that application can be used to determine an analyte, e.g. a bacterium, which reduces a reducible compound thereby releasing a detectable species, e.g. a colored or fluorescent dye, at a pH of 9 or less.

While the assays of Belly et al represent a significant advance in the art, it is desirable to improve the sensitivity of the assays even further to extend their usefulness with analytes at very low concentrations. It is generally known that assays using fluorescent dyes are more sensitive than those using colorimetric dyes. A variety of fluorescent assays have been developed, most of which use coumarin or unbelliferone derivatives as the fluorescent dyes. In the Belly et al application, 4-methylumbelliferone, a representative umbelliferone derivative, was attached to a quinone nucleus to form a reducible compound according to that invention. However, our studies have shown that the resulting compound had limited stability to light (see Example 13 below).

Other known fluorogens present other problems. Some fluorescent dyes can be used only at high pH (greater than 9). They can not be used in biological assays which are normally carried out at lower pH. Further, coumarin or umbelliferone dyes, emit fluorescence at wavelengths at which spectral interferents can be significant, i.e. at wavelengths below 500 nm. This characteristic further limits their usefulness in biological assays.

Recently, improved fluorescent unbelliferone derivatives have been described (Wolfbeis et al, *Bull. Chem. Soc. Japan*, 58:731, 1985) and used in an acid phosphatase assay (*Anal. Biochem.*, 143:146, 1984). Some of these dyes are reported to have pKa values of about 6, and fluorescence emissions at 595 nm (at pH 9). However, these dyes exhibit absorption below about 500 nm (one dye absorbs at 505 at pH 9), i.e. in the same region that some serum components, such as hemoglobin and bilirubin, have strong spectral absorptions.

Hence, there is a need for a highly sensitive assay which is not subject to the problems noted above.

SUMMARY OF THE INVENTION

The problems noted above are overcome by using a substituted or unsubstituted fluorescent compound selected from the group consisting essentially of

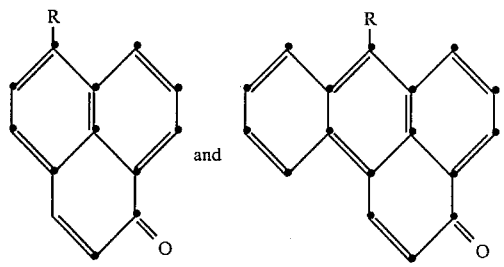

wherein R is hydroxy, mercapto or amino for staining or analytical determinations.

This invention also provides a composition which comprises a reducible compound of the structure CAR—(R¹)$_n$ wherein CAR— is a substituted or unsubstituted aromatic or quinone nucleus, R¹ comprises a fluorescent moiety derived from one of the compounds described above wherein R is hydroxy or mercapto, and n is 1 or 2, provided said reducible compound is capable of being reduced at a pH of 9 or less to release said fluorescent moiety, and further provided that when $R^1$ is replaced with H, CAR—(H)$_n$ has an $E_{\frac{1}{2}}$ of at least about $+100$ mV when measured in water.

Further, a dry analytical element for the determination of an analyte comprises an absorbent carrier material and contains the reducible compound described above.

Still further, this invention provides a method for the determination of an analyte comprising the steps of:
A. at a pH of 9 or less, contacting a sample of a liquid suspected of containing an analyte with the reducible compound described above, and
B. detecting the fluorescent moiety released when the compound is reduced as a result of the presence of the analyte.

This invention also provides a method for staining comprising contacting a biological specimen with a fluorescent compound described above.

The assay of this invention is rapid and highly sensitive to analytes even at low concentrations. It can be used at physiological pH to determine living organisms while avoiding spectral interferents generally encountered in biological specimens because the fluorescent dyes used absorb and emit at generally longer wavelengths than fluorescent dyes of the known assays.

These advantages are achieved by using certain phenalenone and benzphenalenone compounds having maximum absorptions above about 530 nm and maximum emissions at least about 580 nm. These compounds can be readily attached to carriers, such as benzoquinone compounds, to provide releasable compounds. When attached to carriers, the dyes are shiftable, i.e. they fluoresce at different wavelengths when attached than when released. In addition, these compounds can be used to advantage to stain biological specimens such as cells or tissue. The preferred dyes used in this invention have a pKa which is advantageously below about 6 and thus exhibit maximum fluorescence over the pH range of 6 to 9.

BRIEF DESCRIPTION OF THE DRAWING

The FIGURE is a graphical plot of the change in relative fluorescence versus time in minutes for an assay for flucose-6-phosphate dehydrogenase as described in Example 8 below.

DETAILED DESCRIPTION OF THE INVENTION

Figure 1:
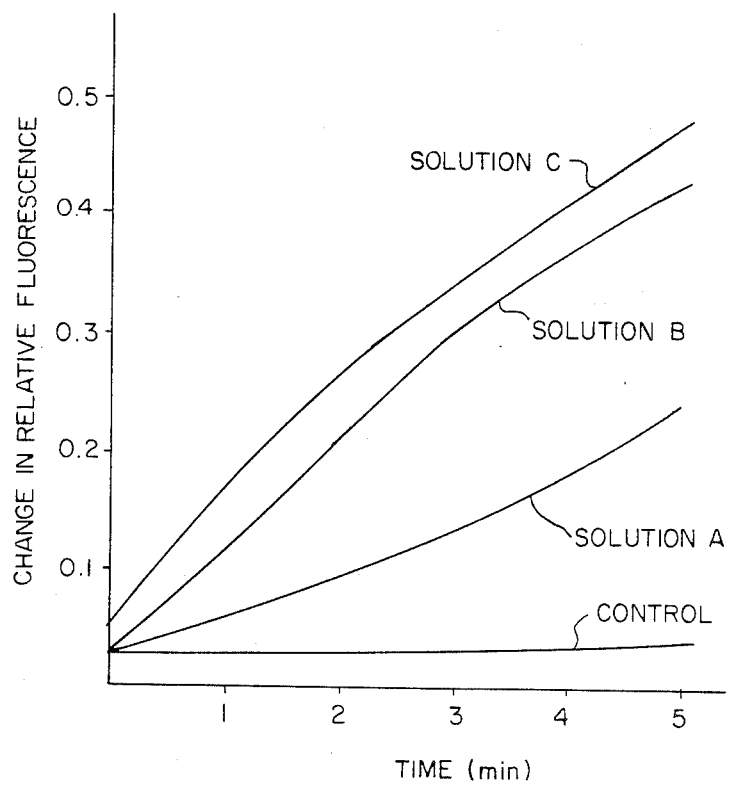

The fluorescent compounds useful in the practice of this invention are substituted or unsubstituted phenalenone or benzphenalenone dyes selected from the group consisting essentially of

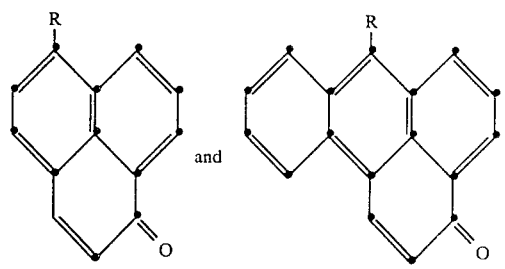

wherein R is hydroxy, mercapto or amino [HN(R')—] or salts thereof (i.e. acid salts, e.g. hydrochloride, sulfate, perchlorate, tetrafluoroborate or p-toluene-sulfonate). R' is hydrogen, substituted or unsubstituted alkyl (preferably of 1 to 10 carbon atoms, e.g. methyl, isopropyl, hexyl, benzyl, chloro benzyl, etc.), substituted or unsubstituted cycloalkyl (preferably of 5 to 12 carbon atoms, e.g. cyclopentyl, cyclohexyl, etc.), substituted or unsubstituted phenyl (e.g. p-alkylphenyl, etc.), or a substituted or unsubstituted heterocyclic moiety (e.g. pyridyl, thienyl, etc.). Preferably, R is hydroxy or amino wherein R' is hydrogen or substituted or unsubstituted lower alkyl of 1 to 3 carbon atoms.

Representative fluorescent compounds useful in this invention include:

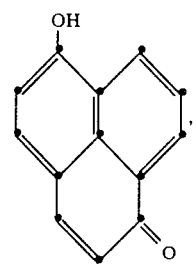

I.

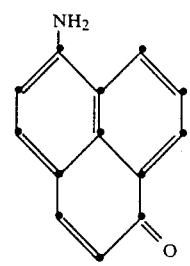

II.

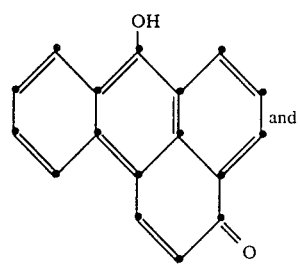

III.

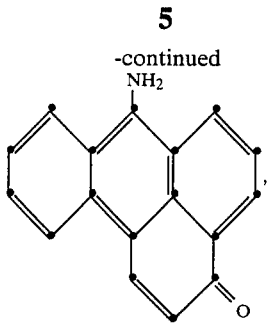

IV.

with compounds I and II being particularly useful. Methods for preparing these compounds are described below. The benzphenalenone compounds III and IV are novel dyes.

These compounds can have one or more substituents other than those specifically illustrated in the formulae at one or more positions on the fused rings as long as the substituents do not adversely affect their fluorescence or pKa values, including substituted or unsubstituted alkyl (preferably of 1 to 12 carbon atoms, e.g. methyl, ethyl, benzyl, etc.), substituted or unsubstituted hydroxyalkyl (preferably of 1 to 12 carbon atoms, e.g. hydroxymethyl, 2-hydroxyethyl, etc.), substituted or unsubstituted alkoxycarbonyl (preferably of 2 to 12 carbon atoms, e.g. methoxycarbonyl, ethoxycarbonyl, etc.), halo (e.g. fluoro, chloro, bromo), cyano, carboxy, acyl, substituted or unsubstituted arylsulfonyl (preferably of 6 to 10 carbon atoms, e.g. phenylsulfonyl, tolylsulfonyl, etc.), substituted or unsubstituted alkylsulfonyl (preferably of 1 to 6 carbon atoms, e.g. methylsulfonyl, ethylsulfonyl, etc.), and other substituents known to one skilled in the art.

Compounds I and II noted above can be prepared as described, for example, by Cooke et al in the *Australian J. Chem.*, 11, pp. 230-235 (1958) and Solodar et al in *Zhurnal Organicheskoi Khimii*, 16(5), pp. 1062-1064 (1980). Novel compounds III and IV noted above can be prepared by procedures described in Examples 2 and 3 below.

The fluorescent compounds useful in this invention can be kept and used in nonbuffered or buffered aqueous solutions. Preferred compounds I and II can be kept and used as buffered aqueous solutions due to their water solubility. Further, compounds II and IV can be converted to their amine salts, and the salts can be kept and used as aqueous solutions. The pH of the solution is generally buffered at 9 or less with one or more appropriate buffers. Useful buffers are readily determined by one skilled in the art, and include phosphates, borates and organic buffers as reported by Good et al in *Biochemistry* 5, 467 (1966) and *Anal. Biochem.*, 104, 300 (1980). The solution is preferably buffered to a pH of 6.5-8.

In one embodiment of the invention, the fluorescent compounds can be used to stain biological specimens, e.g. tissues and cells, and for cell cytometry.

In another embodiment, the fluorescent compounds can be blocked to form dye precursors. When blocked, the compounds are shiftable, the same as when attached to carriers (described below). The blocked dyes can be subjected to a suitable treatment or condition which will release the fluorescent dye from a blocking group during an assay. For example, the dye precursor can be acted upon chemically, hydrolytically or enzymatically by an analyte or other reagent. The fluorescent moiety can be released using hydrolyzable substrates as described in Babb et al U.S. Ser. No. 824,756, identified above.

In still another and preferred embodiment, the fluorescent moiety is released from a reducible compound. While attached to the reducible compound, the fluorescent moiety has absorption and emission spectra different from the absorption and emission spectra it exhibits when released. The emission spectrum upon release is generally at longer wavelengths, i.e. at least about 580 nm.

More particularly, the reducible compounds useful in this invention have the structure CAR—(R$^1$)$_n$ wherein CAR— represents a substituted or unsubstituted aromatic or quinone nucleus, R$^1$ comprises the fluorescent moiety defined above, and n is 1 or 2.

Examples of such nuclei are presented below. Further, when R$^1$ is replaced by H, CAR—(H)$_n$ has a reduction potential (E$_{\frac{1}{2}}$) of at least about +100 mV when measured in water. This E$_{\frac{1}{2}}$ value facilitates the reduction and subsequent release of the shiftable detectable species from the compound at physiological pH (i.e. 9 or less). Such measurements are made according to standard electrochemical techniques using either differential pulse polarography or cyclic voltametry (see, e.g. Sawyer and Roberts, Jr., *Experimental Electrochemistry for Chemists*, John Wiley & Sons, New York, 1974). Preferably, the E$_{\frac{1}{2}}$ is from about +100 mV to about +400 mV as measured in water. Further details of measuring the E$_{\frac{1}{2}}$ are described below prior to Table I. The desired E$_{\frac{1}{2}}$ is achieved by appropriate electron withdrawing groups on the CAR— nucleus, or by a combination of a fused ring attached to the nucleus and electron withdrawing groups.

Examples of useful reducible compounds are illustrated below without intending to limit this invention.

In one embodiment, the reducible compounds can be reduced to provide a detectable species through quinonemethide formation, similar to the described by Van de Sande in *Angew. Chem. Int. Ed. Engl.* 22, pp. 191-209 (1983) and U.S. Pat. No. 4,232,107 (issued Nov. 4, 1980 to Janssens), but which have the desired E$_{\frac{1}{2}}$ properties.

In another embodiment, useful reducible compounds include sulfilimides and sulfenylsulfonamides similar to those described in page 206 of the Van de Sande reference noted above, but which have the desired E$_{\frac{1}{2}}$ properties.

In a preferred embodiment, the reducible compounds are RIND compounds, i.e. reducible compounds capable of undergoing intramolecular nucleophilic displacement at physiological pH to release one or more fluorescent moieties when a nucleophilic group is generated by at least a one electron reduction of the compound. In other words, such displacement occurs when the RIND compound is reduced by a suitable reductant. The distinction of these RIND compounds over the many similar benzoquinone compounds used in the photographic art is that the RIND compounds have a higher E$_{\frac{1}{2}}$ value, thereby facilitating their reduction and subsequent release of a fluorescent moiety (e.g. a dye). This release is very efficient in that, for most of the compounds, at least 50% of the detectable species is released within 30 minutes at about pH 7. These RIND compounds are particularly useful because they release the fluorescent moiety rapidly, allowing for a rapid assay. Similar photographic compounds have lower E$_{\frac{1}{2}}$ values and either release dye only at high pH (13-14), or release dye very inefficiently (i.e. slowly) at physiological pH. Such compounds are described in U.S. Pat. Nos. 4,108,850 (issued Aug. 22, 1978 to Fields et al), 4,139,379 (issued Feb. 13, 1979 to Chasman et al) and 4,144,306 (issued Mar. 13, 1979 to Figueras). When a RIND compound is reduced, e.g. in a clinical chemistry assay, the fluorescent moiety is released and diffuses throughout a solution, or within the layers of an analytical element efficiently (i.e. quickly).

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electrophilic groups juxtaposed in the three-dimensional configuration of the molecule in close proximity whereby the intramolecular reaction can take place and a ring is formed having from 4 to 7 atoms, and preferably having 5 or 6 atoms.

The rate of nucleophilic displacement is substantially zero prior to reduction of the RIND compound. Hence, the RIND compounds are stable prior to that reduction.

Particularly useful RIND compounds are those which have the structure CAR—$R^1$ wherein CAR— is

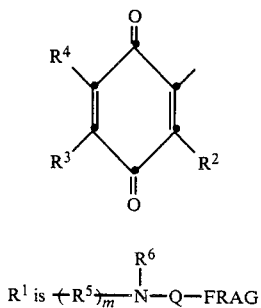

wherein m is 0 or 1, and preferably 1. $R^5$ is substituted or unsubstituted alkylene, preferably of 1 or 1 carbon atoms in the backbone (e.g. methylene, ethylene, alkoxymethylene, etc.). Most preferably, $R^5$ is methylene. Q is carbonyl or thiocarbonyl and preferably carbonyl.

$R^6$ is methyl.

FRAG is a fluorescent moiety as defined above derived from a substituted or unsubstituted phenalenone or benzphenalenone compound. This species is released in an amount which can be directly related to the amount of reductant present.

FRAG is linked to Q by means of a single bond through a bivalent monoatom linkage which is a part of FRAG. Preferably, the monoatom linkage is oxy or thio, and most preferably it is oxy.

$R^2$, $R^3$ and $R^4$ in the above quinone structure are independently hydrogen, substituted or unsubstituted alkyl of 1 to 40 carbon atoms (e.g. methyl, ethyl, hydroxymethyl, methoxymethyl, benzyl, etc.) substituted or unsubstituted aryl (e.g. phenyl, naphthyl, methylnaphthyl, p-nitrophenyl, m-methoxyphenyl, phenylsulfonamido, etc.) or an electron withdrawing group which generally has a positive Hammett sigma value, and preferably has a sigma value greater than about 0.06. Hammett sigma values are calculated in accordance with standard procedures described, e.g. in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (e.g. fluoro, bromo, chloro, iodo), trihalomethyl (e.g. trifluoromethyl, trichloromethyl, etc.), trialkylammonium, carbonyl, carbamoyl, sulfonyl, sulfamoyl, esters and others known in the art. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of fluorescent moiety molecules to original RIND compound molecules.

Alternatively, $R^3$ and $R^4$, taken together, can represent the carbon atoms necessary to complete a substituted or unsubstituted fused carbocyclic ring attached to the quinone nucleus. For example, such a ring (mono- or bicyclic) can have from 4 to 8, and preferably from 5 to 7, carbon atoms in the backbone.

Representative novel RIND compounds of this invention are listed in Table I below in reference to the following structure:

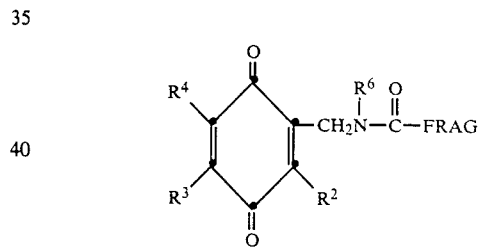

The $E_{\frac{1}{2}}$ values in Table I were determined for the quinone nucleus of this structure having a hydrogen atom in place of

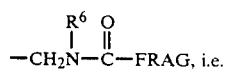

i.e.

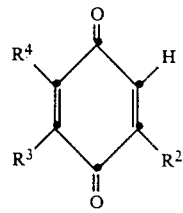

The $E_{\frac{1}{2}}$ values were measured in an aqueous emulsion of the quinone dissolved in N,N-dimethylformamide, a nonionic surfactant (TRITON X-100) and sodium phosphate buffer (pH 7). A normal hydrogen electrode was used as a standard.

TABLE I

| RIND Compound | $R^6$ | $R^2$ | $R^4$  $R^3$ | FLAG | $E_{\frac{1}{2}}(mV)$ |
|---|---|---|---|---|---|
| I. | —CH₃ | (phenyl with —CN) | $R^3$ and $R^4$ together form (cyclohexene fragment) | (naphthoquinone with —O—) | +220 |
| II. | —CH₃ | (phenyl) | $R^3$ and $R^4$ together form (propenyl fragment) | (naphthoquinone with —O—) | +222 |
| III. | —CH₃ | (phenyl with Cl, Cl) | $R^3$ and $R^4$ together form (cyclohexene fragment) | (naphthoquinone with —O—) | +236 |
| IV. | —CH₃ | (phenyl with NO₂) | $R^3$ and $R^4$ together form (cyclohexene fragment) | (naphthoquinone with —O—) | +214 |
| V. | —CH₃ | (phenyl with NO₂) | $R^3$ and $R^4$ together form (cyclohexene fragment) | (naphthoquinone with —O—) | +236 |
| VI. | —CH₃ | (phenyl with —SO₂NH(CH₃)₂) | $R^3$ and $R^4$ together form (cyclohexene fragment) | (naphthoquinone with —O—) | +212 |

The RIND compounds useful in this invention are prepared using a sequence of individually known reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of the FRAG moiety with the carbamoyl chloride. Representative preparations are provided in Examples 4 and 5 below.

Other RIND compounds useful in the practice of this invention include those having the appropriate $E_{\frac{1}{2}}$ values and the structure CAR$(R^1)_n$ wherein:

(1) CAR- is a substituted or unsubstituted nucleus of a 1,2-naphthoquinone, 1,2,-, 1,4- or 9,10-anthraquinone, 4,4'-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more fused rings as described above for $R^3$ and $R^4$.

$R^1$ is

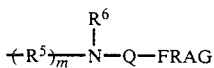

as defined above, and n is an integer of 1 or 2.

(2) CAR- is

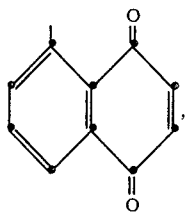

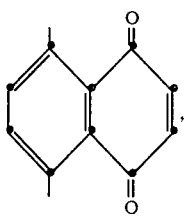

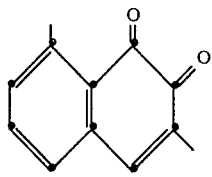

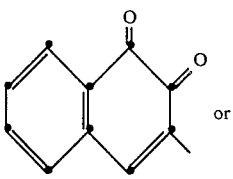

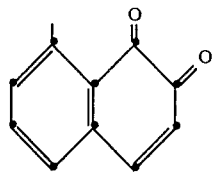

any of which can be substituted with one or more electron withdrawing groups as described above for $R^2$, $R^3$ and $R^4$. $R^1$ is

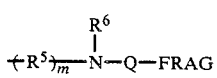

as defined above, and n is 1 or 2.

(3) CAR- is a substituted or unsubstituted nitrobenzenoid nucleus of the structure

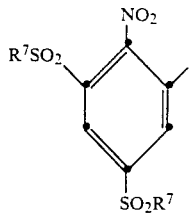

wherein $R^7$ is substituted or unsubstituted alkyl of 1 to 20 carbon atoms (e.g. methyl, ethyl, methoxymethyl, isopropyl, dodecyl, hexadecyl, octadecyl, etc.), and $R^1$ is

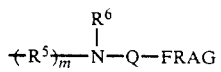

as defined above and n is 1. These compounds are similar to some described in U.S. Pat. No. 4,139,379 (issued Feb. 13, 1979 to Chasman et al).

All of these reducible compounds can be prepared using techniques and starting materials known in the art or readily apparent to a skilled synthetic chemist.

Generally, the reducible compounds described herein have limited water solubility. Hence, it is best, when using them in an aqueous environment, to prepare a dispersion of the compound prior to use, e.g. in a coating formulation. Such dispersions generally comprise the reducible compound, an aqueous buffer solution and either a surfactant or a water-miscible organic solvent for the compound, or both.

Surfactants which are useful in the practice of this invention include any surfactants which do not inhibit compound reduction. Generally, for detection of living cells, the useful surfactants are nonionic surfactants, including, for example, alkylarylpolyethoxy alcohols (e.g. TRITON X-100 and X-305 available from Rohm & Haas, Philadelphia, Pa., U.S.A.), p-alkylaryloxypolyglycidols (e.g. SURFACTANT 10G available from Olin Corp., Stamford, Conn., U.S.A.), TWEEN 80 (available from ICI Americas, Inc., Wilmington, Del., U.S.A.), and others known to one skilled in the art.

Useful water-miscible organic solvents include alcohols (e.g. methanol, ethanol, propanol, etc.), N,N-dimethylformamide, dimethyl sulfoxide, acetonitrile, hexamethylenephosphoramide and the like. The particular solvent to be used for a particular reducible compound can be readily determined by routine experimentation.

A dispersion can be prepared in the following general manner with the particular details of such a preparation illustrated in Examples 4 and 5 below. The reducible compound is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of dispersion. This preparation is generally carried out at room temperature.

These dispersions contain a buffer in an amount effective to maintain a physiological pH (9 or less). The concentration of buffer in the dispersion can vary widely, but is generally from about 0.01 to about 0.5 molar. Representative buffers are described above.

The reducible compound described herein are useful in compositions for analytical determination (i.e. qualitative, semi-quantitative or quantitative detection) of aqueous and nonaqueous liquids, e.g. biological fluids, manufacturing processes, waste-water, food stuffs, etc. Determinations can be made of various analytes via a single reaction or a sequence of reactions which bring about reduction of the compound and release of the fluorescent moiety. The various analytes include living cells (e.g. bacteria, yeast, white blood cells, fungi, etc.), enzymes (e.g. lipase, glucose oxidase, lactate oxidase, creatine kinase, α-glycerophosphate oxidase, lactate dehydrogenase, pyruvate dehydrogenase, glucose-6-phosphate dehydrogenase, alanine aminotransferase, aspartate aminotransferase and other NADH-based, FADH-based or oxidase-based assays which include dehydrogenase or reductase enzymes), biological or chemical reductants other than living cells (e.g. ascorbates, cysteine, glutathione, thioredoxin, etc.), metabolizable substances (e.g. glucose, lactic acid, triglycerides, cholesterol, etc.), immunoreactants (e.g. antigens, antibodies, haptens, etc.).

The compositions can be used to monitor flavin-linked dehydrogenases and oxidases, including (NAD—NADH)—, (FAD—FADH)— and (NADP—NADPH)—based reactions. In such instances, the reducible compound can be used to provide a fluorescent dye in place of NADH, FADH or NADPH.

The reducible compounds described herein are particularly useful in detecting or quantifying living cells in biological samples. Although any biological sample suspected of having living cells therein (e.g. food, tissue, ground water, cooling water, pharmaceutical products, sewage, etc.) can be analyzed for bacteria, yeast, fungi, etc. by this invention, the invention is particularly useful for bacterial detection in aqueous liquids, such as human and animal fluids (e.g. urine, cerebral spinal fluid, blood and the like as well as stool secretions) and suspensions of human or animal tissue. The practice of this invention is particularly important for detection of urinary tract infections in urine (diluted or undiluted).

When determining living cells using the reducible compounds, it is preferable for rapid dye release that the living cells interact with an electron transfer agent (herein ETA). The presence of an ETA may provide more efficient dye release for analytical determinations of nonliving analytes. The ETA is a mobile compound which acts as an intermediary between the substance being determined (e.g. living cell) and the reducible compound.

In general, the ETA compounds useful in the practice of this invention have an $E_{\frac{1}{2}}$ in the range of from about $-320$ to about $+400$ mV as measured in aqueous buffer (pH 7) versus the normal hydrogen electrode using a differential pulse polarographic technique with a PAR Potentiostat (Princeton Applied Research, Princeton, N.J.). In general, the potential of the ETA should be more positive than the potential of the substance to be determined (i.e. analyte) and less positive than the potential of the RIND compound. That is, the ETA should be more easily reduced than the analyte and less easily reduced than the reducible compound. They are generally present at a concentration that is dependant upon the concentration of the analyte, and preferably at a concentration of from about $1 \times 10^{-3}$ molar to about $1 \times 10^{-7}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds useful in the practice of this invention which provide further advantages of low background are those which are the subject of U.S. Ser. No. 699,374 filed Feb. 7, 1985 by Mura et al. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2-hydroxymethyl-1,4-naphthoquinone and 2-(2-hydroxyethyl)-1,4-naphthoquinone.

The determination of living cells, and particularly of bacterial cells, is often carried out in the presence of a nutrient for those cells although its presence is not essential. Any nutrient medium can be used which contains useful carbon, and optionally nitrogen, sources. Suitable nutrient media having proper components and pH are well known in the art.

The present invention is adaptable to either solution or dry assays. In a solution assay, a solution (or aqueous dispersion) containing a reducible compound, and preferably an ETA, can be prepared and contacted with a liquid test sample containing the living cells or analyte to be determined by mixing. The ETA can also be mixed with the test sample prior to mixing with the reducible compound. Generally the reducible compound is mixed with the test sample in a suitable container (e.g. test tube, petri dish, beaker, cuvette, test device, etc.). The resulting solution (or dispersion) is gently mixed and incubated for a relatively short time (i.e. up to about 30 minutes) at a temperature up to about 40° C., and generally from about 20° to about 40° C. The test sample is then evaluated by measuring the resulting fluorescent dye with suitable detection equipment.

The solution assay can also be carried out by contacting a porous, absorbent material, e.g. paper strip, containing the test sample with a dispersion of the reducible compound. The analyte in the test sample can migrate from the porous material into the dispersion and initiate the analytical reactions needed for determination. In solution assays, the amount of reducible compound present is at least about 0.001, and preferably from about 0.01 to about 1.0, millimolar. Other reagents can be present in amounts readily determined by one skilled in the art.

Alternatively, the method of this invention can be practiced with a dry analytical element. Such an element can be an absorbent carrier material, i.e. a thin sheet or strip of self-supporting absorbent or bibulous material, such as filter paper or strips, which contains the reducible compound or a dried residue of the dispersion comprising same. Such elements are known in the art as test strips, diagnostic elements, dip sticks, diagnostic agents and the like.

When employed in dry analytical elements, the reducible compounds described herein can be incorporated into a suitable absorbent carrier material by imbibition or impregnation, or can be coated on a suitable absorbent carrier material. Alternatively, they can be incorporated in the element during an assay. Useful carrier materials are insoluble and maintain their structural integrity when contacted with water or physiological fluids such as urine or serum. Useful carrier materials can be prepared from paper, porous particulate structures, cellulose, porous polymeric films, wood, glass fiber, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

A dry assay can be practiced to particular advantage with an analytical element comprising a support having thereon at least one porous spreading zone as the absorbent carrier material. The reducible compound can be in the spreading zone or in a different zone (e.g. reagent zone, registration zone, hydrophilic zone, etc.). The spreading zone can be prepared from any suitable fibrous or non-fibrous material or mixtures of either or both.

The spreading zone can be prepared using fibrous materials, either mixed with a suitable binder material or woven into a fabric, as described in U.S. Pat. No. 4,292,272 (issued Sept. 29, 1981 to Kitajima et al), polymeric compositions (e.g. blush polymers) or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al), and 4,430,436 (issued Feb. 7, 1984 to Koyama et al) and Japanese Patent Publication 57(1982)-101760 (published June 24, 1982). It is desired that the spreading zones be isotropically porous, meaning that the porosity is the same in each direction in the zone as created by interconnected spaces or pores between particles, fibers, polymeric strands, etc.

The dry analytical element of this invention can be a single self-supporting absorbent carrier material containing a reducible compound and any other desired reagents for a particular use, but preferably such material is carried on a suitable nonporous support. Such a support can be any suitable dimensionally stable, and preferably, transparent (i.e. radiation transmissive) film or sheet material which transmits electromagnetic radiation of a wavelength between about 200 and about 900 nm. A support of choice for a particular element should be compatible with the intended mode of detection and inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, subbing zone, etc. The zones are generally in fluid contact with each other, meaning that fluids, reagents and reaction products can pass between superposed regions of adjacent zones. Preferably, the zones are separately coated superposed layers, although two or more zones can be located in a single layer. Besides the Przybylowicz et al and Pierce et al patents noted above, suitable element formats and components are described also, for example, in U.S. Pat. Nos. 4,042,335 (issued Aug. 16, 1977 to Clément) and 4,144,306 (noted above) and U.S. Pat. No. Re. 30,267 (reissued May 6, 1980 to Bruschi).

In the elements of this invention, the amount of the reducible compound can be varied widely, but it is generally present in a coverage of at least about 0.01, and preferably from about 0.05 to about 0.2, $g/m^2$. Optional, but preferred reagents (e.g. ETA, nutrient, buffer, etc.) are generally present in the following coverages:

ETA: generally at least about 0.001, and preferably from about 0.01 to about 1, $g/m^2$, nutrient: generally at least about 0.05, and preferably from about 0.1 to about 2, $g/m^2$ (used only in living cell detection), buffer (pH$\leq$9): generally at least about 0.1, and preferably from about 0.5 to about 2, $g/m^2$, and surfactant: generally at least about 0.1, and preferably from about 0.2 to about 5, $g/m^2$.

One or more of the zones can contain a variety of other desirable, but optional, components, including activators, binders (generally hydrophilic), coupler solvents, etc. as is known in the art, as well as any reagents needed for assay of a particular analyte.

In one embodiment of this invention, an element for detection of microorganisms (e.g. yeast, fungi, bacteria, etc.) in an aqueous liquid comprises an electron transfer agent and a reducible compound, both of which are described above. It is desirable that these elements also contain a nutrient for the living cells and a buffer which maintains physiological pH during the assay (e.g. when contacted with a 1–200 $\mu l$ sample of test liquid). Such an element can be used to detect bacteria, for example, in a urine sample (e.g. one pretreated to eliminate reduction interferents) by physically contacting the sample and element in a suitable manner, and detecting the fluorescent dye released from the reducible compound as a result of the presence of bacteria at the appropriate wavelength greater than about 590 nm.

In another embodiment of this invention, an element is used for the determination of a nonliving biological or chemical analyte in an aqueous liquid, and comprises an interactive composition which is capable of providing a fluorescent dye upon interaction with the analyte. This composition comprises a reducible compound which releases a fluorescent dye when reduced to provide the dye, and optionally an ETA, a nonionic surfactant and a buffer which maintains physiological pH during the assay, all of which are described above. Examples of such analytes are described above. The elements contain interactive compositions having suitable reagents which effect reduction of the reducible compound. The amount of fluorescent dye detected can be correlated to the amount of analyte present in the liquid sample A pretreatment step to remove interferences or to concentrate cells prior to assay may be desirable.

The element of this invention is also useful for determining other reductants such as ascorbate (ascorbic acid and alkali metal salts), cysteine, glutathione, thioredoxin and the like.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and contacting it with a sample (e.g. 1–200 $\mu l$) of the liquid to be tested which mixes with the reagents in the element. Such contact can be accomplished in any suitable manner, e.g. dipping or immersing the element into the sample or, preferably, by spotting the element by hand or machine with one or more drops of the sample with a suitable dispensing means.

After sample application, the element is exposed to any conditioning, such as incubation, heating or the like, that may be desirable to quicken or otherwise facilitate obtaining any test result.

Detection of an analyte or living cell is achieved when the reducible compound is reduced releasing a fluorescent dye which can be detected in a suitable manner. Determinations can be made at the maximum wavelength of the dye, or at a wavelength other than the maximum wavelength.

In the examples which follow illustrating the practice of the invention, the materials used were obtained as follows:

ZONYL FSN surfactant from Dupont Co. (Wilmington, Del., U.S.A.),

TRITON X-100 surfactant from Rohm and Haas (Philadelphia, Pa., U.S.A.),

DAXAD 30 surfactant from W. R. Grace Co. (Lexington, Mass., U.S.A.), the bacterial microorganisms from American Type Culture Collection (ATCC in Rockville, Md., U.S.A.), phenazine methosulfate, glucose-6-phosphate, nicotinamide adenine dinucleotide phosphate, glucose-6-phosphate dehydrogenase, nicotinamide adenine dinucleotide, reduced form and ascorbic acid from Sigma Chemical Co (St. Louis, Mo., U.S.A.), brain heart infusion media and yeast extract from Difco Labs (Detroit, Mich., U.S.A.), and the remainder were obtained from Eastman Kodak Co. (Rochester, N.Y., U.S.A.) or prepared using known starting materials and procedures.

In the following examples, the identity and purity of intermediate compounds were determined by infrared (IR) spectra as measured in a commercially available Perkin-Elmer 137 spectrophotometer [sharp(s) or broad(b) bands yielding structural information are reported in reciprocal centimeters (cm$^{-1}$)] or by nuclear magnetic resonance (NMR) spectra measured in a commercially available Varian T60 NMR spectrophotometer [chemical shifts reported in δ values in ppm to tetramethylsilane at broad (b), singlet(s), multiplet(m) or broad singlets(bs) peaks]. The identity and purity of final products were determined by IR, NMR spectroscopy and elemental analysis.

The identified RIND compounds are the reducible compounds listed in Table I above.

EXAMPLE 1

Solutions of Fluorescent Dye I

Fluorescent compound I, identified above, can be kept and used as either a nonbuffered or buffered aqueous solution. An aqueous solution was prepared by adding dye (2 mg) to distilled water (20 ml), and sonicating the mixture until a solution was obtained (about 1 minute). The buffered solution was prepared by adding 0.1 ml of the aqueous solution to 2.9 ml of 0.05 molar potassium phosphate buffer (pH 7.8).

EXAMPLE 2

Preparation of Fluorescent Compound III

Step A: Anthrone (75 g) was dissolved in 400 ml of trimethylphosphate by heating to 120° C. Sodium hydroxide solution (50 ml of 50% solution) was added in 2 ml portions. At first, the temperature rose to 125°–130° C., then declined to 105°–110° C. At the end of the reaction, vigorous boiling occurred. On cooling to 90° C., the mixture set-up to a solid. Water was added and the light yellow product was collected, washed with water and recrystallized directly from ethyl alcohol. There was obtained 68 g of Intermediate A having a m.p. of 92°–94° C. Mass spectral analyses confirmed the structure.

Step B: Intermediate A (6 g) was dissolved in N,N-dimethylformamide (DMF, 25 ml). The mixture was cooled and treated with phosphorous oxychloride (3.5 g) in portions with stirring. The resulting solution was heated at 100° C. for two hours and then allowed to stand in a stoppered flask. The resulting mixture was poured into water containing sodium acetate. The yellow product was collected and recrystallized from acetone. The yield was 4 g of Intermediate B. Mass spectral analyses confirmed the structure.

Step C: Sodium methoxide (15 g) was dissolved in 300 ml of dry methanol and this solution was chilled to 0° C. A solution of Intermediate B (24 g) and triethylphosphonoacetate (25 g) in warm DMF (300 ml) was added and the mixture was heated under reflux for three hours. Water (100 ml) was then added and the solution was refluxed for an additional hour. The solution was diluted to 1200 ml with water and concentrated hydrochloric acid was added until the mixture was acidic (pH 2). The mixture was then cooled, the solid was collected and recrystallized from ethyl alcohol (250 ml). There was obtained 18 g of Intermediate C. Infrared and nuclear magnetic resonance analyses confirmed the structure.

Step D: Intermediate C (18 g) was dissolved in dilute sodium carbonate solution (500 ml) and the solution was filtered. The filtrate was treated with a catalytic amount of 10% palladium on carbon and the resulting mixture was shaken under hydrogen in a Parr shaker. After the theoretical amount of hydrogen was absorbed, the catalyst was removed by filtration and the filtrate was acidified with concentrated hydrochloric acid. The product was collected and recrystallized from methanol to give 10 g of Intermediate D. Infrared and mass spectral analyses confirmed the structure.

Step E: Intermediate D (3 g) dissolved in dichloromethane (50 ml) was treated with phosphorous pentachloride (2.5 g) and the mixture was refluxed for thirty minutes. Aluminum chloride (3 g) was then added in small portions and this mixture was stirred and heated under reflux was five hours. The mixture was poured into dilute hydrochloric acid and this solution was extracted with ethyl acetate. After drying, the solvent was removed under reduced pressure to give 3 g of a red semi-solid. The material was taken up in 4:1 toluene-:ethyl acetate. The mixture was cooled and the insoluble material was collected to give 0.3 g of Compound III identified above. Mass spectral analyses confirmed the structure.

EXAMPLE 3

Preparation of Fluorescent Compound IV

Compound IV can be prepared from Compound III using the procedures described by Solodar et al, Zhurnal Organicheskoi Khimii, 16(5), 1062 (1980).

EXAMPLE 4

Preparation of RIND I and Buffered Dispersion Containing Same

Step A: A mixture of p-cyanoaniline (23.5 g, 0.2 mole), concentrated HCl (80 ml) and water (200 ml) was warmed until solution was obtained, then cooled to 0°-5° C. Sodium nitrite (13.8 g, 0.2 mole), dissolved in H$_2$O (25 ml), was added slowly to prevent any rise in temperature. After stirring at 0° C. for one hour, the resulting diazonium salt was added slowly to a mechanically stirred mixture of p-benzoquinone (25.9 g, 0.23 mole), sodium acetate (100 g, 1.2 mole), and ice water (2300 ml) in a 4 liter beaker. The goldencolored heterogeneous mixture was stirred in an ice bath for four hours and slowly warmed to room temperature. The solid was isolated by filtration, washed repeatedly with water, then dried and recrystallized from acetonitrile to give 21.7 g of Intermediate A.

Step B-F: Intermediate A was then treated according to the procedures described in Example 1, Steps 2a-6 of the Belly et al application, U.S. Ser. No. 824,766 noted above and herein incorporated by reference.

Step G: Intermediate F (17.3 g, 43.7 mmole) was added in portions over 45 minutes to a solution of Compound I (6.6 g, 33.6 mmole) and 4-dimethylaminopyridine (catalytic amount) in pyridine (175 ml). The reaction mixture was stirred at 25° C. for 15 hours under a nitrogen atmosphere. The resulting mixture was poured into hydrochloric acid and ice water (3 liters) to precipitate a yellow solid. The solid was collected by filtration, washed with water and dried under vacuum. Chromatography (silica, 90:10, dichloromethane:acetone) afforded a yellow foam which was solidified by stirring for 15 minutes in ether (100 ml). The solid was collected and dried to give 13.8 g (74% yield) of RIND I, m.p. 210-213° C. Analysis, calculated for $C_{35}H_{26}N_2O_5$: C, 75.8, H, 4.7, N, 5.1. Found: C, 75.1, H, 4.9, N, 5.0.

Step H: A buffered dispersion of the RIND I compound was prepared as follows: RIND I was dissolved in N,N-dimethylformamide (16 mg per ml). An aliquot of 0.25 ml of this solution was mixed with 0.5 ml of TRITON X-100 surfactant. The resulting solution was then added dropwise to 25 ml of 0.05 molar potassium phosphate buffer (pH 7.5) while the buffer was stirred at room temperature. A clear dispersion resulted.

EXAMPLE 5

Preparation of RIND II and Buffered Solution Containing Same

Rind II was prepared by the following sequence of steps.

Step A: A mixture of 2,5-dimethoxy-4-phenylbenzaldehyde (52.5 g, 0.22 mole), malonic acid (51.8 g, 0.5 mole) and piperdine (2.5 ml) in pyridine (100 ml) was heated at 80° C. for 15 hours. After cooling, the mixture was poured into hydrochloric acid/ice water (2.5 liters). The precipitated yellow solid was collected by filtration, washed with water, and dried on the filter. The product was refluxed in acetonitrile (600 ml) for 30 minutes, the mixture was cooled, and the yellow solid was collected, washed with acetonitrile, and dried on the filter. This product (43.3 g) was suspended in ethanol (1.25 liter), placed in a Parr shaker bottle with 10% palladium on charcoal catalyst and shaken under hydrogen for 3 days. The catalyst was filtered off, and the filtrate was concentrated to yield 35 g of Intermediate A having a m.p. of 143-146° C.

Step B: A mixture of Intermediate A (35 g, 0.12 mole) and oxalyl chloride (23.3 g, 0.18 mole) in dichloromethane (400 ml) was stirred at 25° C. for 8 hours. The solution was concentrated under reduced pressure to yield an orange oil. Two separate portions of dichloromethane (about 50 ml) were added and then removed under reduced pressure. The oil obtained (about 37 g, Intermediate B) was used directly in the next step.

Step C: Intermediate B (about 37 g, 0.12 mole) was dissolved in dichloromethane (400 ml). This solution was cooled in an ice bath and stannic chloride (38 g, 0.15 mole) was added. The reaction mixture was allowed to set at 25° C. for 30 hours, then poured into hydrochloric acid/ice water (3 liters) and stirred for 15 minutes. The layers were separated, and the water layer was washed twice with dichloromethane. The organic layers were combined, dried, and concentrated under reduced pressure to give a solid product. Chromatography on silica with dichloromethane, ether (98:2) gave 28 g of yellow Intermediate C, mp 97-99° C.

Step D: A solution of Intermediate C (28 g, 0.104 mole) in acetic acid (600 ml) and perchloric acid (12 ml) was placed in a Parr shaker bottle with 10% Palladium on charcoal catalyst and shaken under hydrogen for one week. Potassium acetate (about 10 g) was added, then mixture was stirred for 10 minutes, then filtered to remove the catalyst. The filtrate was concentrated under reduced pressure to give a semi-solid product. This product was dissolved in tetrahydrofuran and the solution was poured into ice water. The water was extracted with dichloromethane and the solvent was dried and concentrated. Toluene was added in two separate portions and removed under reduced pressure. There was obtained 23.5 g of Intermediate D.

Step E: Cerric ammonium nitrate (152 g, 0.28 mole) was dissolved in water (325 ml) and added dropwise with stirring over 45 minutes to a solution of Intermediate D in acetonitrile (325 ml). The reaction mixture was allowed to stir and additional 30 minutes. Water (300 ml) was added, and the mixture was extracted with dichloromethane (4×100 ml) and ethyl ether (1×100 ml). The organic layers were combined, dried, and concentrated to yield 24 g of orange oil. A purified sample of the oil solidified, mp 81-82.5° C.

Step F: Intermediate E (24 g, 0.11 mole) was dissolved in tetrahydrofuran (200 ml), placed in a Parr shaker bottle with 10% palladium on charcoal, and shaken under hydrogen for 75 minutes. The catalyst was filtered off under nitrogen, and the filtrate was concentrated to give 23 g of Intermediate F. This product was used directly in the next reaction.

Step G: Intermediate F (23 g, 0.1 mole) and N,N-(diisobutoxymethylene)methylamine (30.9 g, 0.15 mole) in toluene (50 ml) were heated at 90° C. under a nitrogen atmosphere for 3 hours. Thin layer chromatography (silica, dichloromethane:ether, 95:5) showed the presence of starting material. The solvent was removed, N,N-(diisobutoxymethylene)methylamine (1 ml) was added, and the mixture was heated neat for an additional 3 hours. Methanol (50 ml) was added and the mixture was brought to reflux. The mixture was allowed to cool overnight at 0° C. The product was collected, washed with cold methanol, and dried. There was obtained 11.9 g of Intermediate G, mp 212-213° C.

Step H: A mixture of intermediate G (11.9 g, 0.04 mole) and ferric chloride (17.1 g, 0.063 mole) in hydrochloric acid (35 ml), water (35 ml), and methanol (100 ml) was refluxed for 8 hours. The reaction mixture was cooled at 0° C. for several hours and filtered. The filtrate was treated with water (100 ml) and extracted with tetrahydrofuran/dichloromethane (1:1), 3×100 ml. The combined extracts were dried, treated with charcoal, and filtered. The filtrate was concentrated to yield 10.3 g of Intermediate H.

Step I: Intermediate H (10.3 g, 0.034 mole) and triethylamine (6.9 g, 0.068 mole) were dissolved in dichloromethane (100 ml). This solution was added in portions at 0° C. with stirring to dichloromethane (300 ml), which had previously been saturated with phosgene gas. The reaction mixture was allowed to stir at 0° C. for 15 minutes, then allowed to warm to 25° C. over two hours. The solvent was removed under reduced pressure and ethyl ether/tetrahydrofuran (1:1, 100 ml) was added. This mixture was stirred, and the solid was filtered off and washed with ethyl ether/tetrahydrofuran. The filtrate was concentrated to give 11.1 g of product, Intermediate I.

Step J: A suspension of Dye I (2.4 g, 0.013 mole) in pyridine (100 ml) under a nitrogen atmosphere was treated with a catalytic amount of 4-N,N-dimethylaminopyridine and Intermediate I (5 g, 0.015 mole), then stirred in a dark area for 5 hours. The reaction mixture was poured into hydrochloric acid/ice water (2 liters), the solid product was collected, washed with water, and dried under vaccum for 15 hours in a dark area. Chromatography (silica, dichloromethane/acetone, 9:1) yielded 1.3 g of product, RIND II.

Analysis: calculated for $C_{31}H_{23}NO_5$: C, 76.1, H, 4.7, N, 2.9.

Found: C, 74.1, H, 4.8, N, 2.8.

A dispersion of RIND II was prepared by the same procedure described in Example 4.

EXAMPLE 6

Staining of White Blood Cells Using Phenalenone Dyes

This example demonstrates the usefulness of phenalenone dye Compounds I and II for staining white blood cells.

Leukocyte-rich layers (buffy coats) were purified from the blood of healthy adult donors (taken in ACD tubes*) by adding 1.5 ml of Dextran T70 (6% in balanced salt solution) obtained from Pharmacia Fine Chemicals (Piscataway, N.J., U.S.A.) to a 10 ml tube of blood. The tubes were allowed to set for one hour, then the plasma layer was transferred to sterile 15 ml centrifuge tubes and the tubes were filled up to 7.6 ml with PBS solution (8.5 g sodium chloride in 0.05 molar potassium phosphate buffer, pH 7.5). The tubes were then centrifuged at 1000 RPM for ten minutes, the cell pellet was resuspended in 10 ml lysing solution [0.83 g ammonium chloride, 0.1 g sodium bicarbonate and 0.003 g (ethylenedinitrilo)tetraacetic acid disodium salt in 100 ml of $H_2O$, pH 7.2] and the tubes were allowed to set until the solution cleared. The tubes were again centrifuged, the pellet was washed and resuspended in PBS. Cells were counted and adjusted to approximately $10^6$ cells/ml.

*ACD (acid, citrate, dextrose B-D4606) prefilled blood collection tubes were purchased from VWR Scientific (Rochester, N.Y., U.S.A.).

Two hundred microliters of cell suspension were placed in the sample well of a Shandon Cytospin Cytocentrifuge, available from Shandon Southern Instruments, Inc. (Sewickley, Pa., U.S.A.) and centrifuged at maximum speed for ten minutes. The fixed cell preparations were air dried and stained for 1-2 minutes with Compounds I and II (1 mg/ml methanol) and washed with distilled water.

Stained cell preparations were examined under a Zeiss Universal epifluorescence microscope (excitation 546 nm, emission 590 nm). Bright oranged-red fluorescence of the white blood cells were observed with minimal background fluorescence.

EXAMPLE 7

Solution Assay for *Pseudomonas aeruginosa* Using RIND II

The following solutions were used in this assay: an electron transfer agent (ETA) in methanol, 0.01 molar and *Pseudomonas aeruginosa*, grown in brain heat infusion medium and having a concentration of $1\times10^8$ cells/ml.

Solutions were prepared from the following components: 1.5 ml RIND II dispersion prepared as described in Example 4, 1.5 ml potassium phosphate buffer (pH 7.5), 25 μl glucose stock solution (10%) and 25 μl of *Pseudomonas aeruginosa* solution. Twenty-five μl of the appropriate ETA were then added. The control did not contain any ETA. The fluorescence was then measured at 25° C. in a commercially available Farrand spectrofluorometer (excitation, 540 nm, emission, 620 nm) at initial time (when solutions were first mixed) and at 5, 15, and 30 minutes later.

The results, shown in Table II below, indicate that RIND II can be used in a solution assay for *Pseudomonas aeruginosa* using two different electron transfer agents.

TABLE II

| Solution | Relative Fluorescence | | | |
| --- | --- | --- | --- | --- |
| | Initial Time | 5 Min | 15 Min | 30 Min |
| Control | 0.058 | 0.062 | 0.066 | 0.078 |
| TMBQ* | 0.059 | 0.081 | 0.144 | 0.290 |
| DMHBQ** | 0.058 | 0.087 | 0.177 | 0.360 |

*2,3,5-Trimethyl-1,4-benzoquinone
**2,3-Dimethyl-5-hydroxymethyl-1,4-benzoquinone

EXAMPLE 8

Solution Assay for Glucose-6-Phosphate Dehydrogenase Using RIND I

Stock solutions were prepared from the following reagents:

glucose-6-phosphate, (0.1 molar) in distilled water,
nicotinamide adenine dinucleotide phosphate, (0.006 molar) in distilled water,
glucose-6-phosphate dehydrogenase, (0.27 mg) in 2 ml distilled water, and
tris(hydroxymethyl)aminomethane-Mg buffer (TRIS-Mg buffer) was prepared from 0.055 molar Tris.HCl (pH 7.8) and 0.0033 molar magnesium chloride.

A dispersion of RIND I was prepared by dissolving 4 mg of RIND I in 250 μl of N,N-dimethylformamide, adding 0.5 ml of TRITON X-100 surfactant and then adding this solution slowly with stirring to 25 ml of the TRIS-Mg buffer (pH 7.8) solution.

Test solutions were prepared from the following components: 1.5 ml RIND I dispersion, 1.2 ml tris-Mg buffer, 100 μl of stock solution of nicotinamide adenine dinucleotide phosphate, 100 μl of glucose-6-phosphate, and 25 μl of phenazine methosulfate solution (3 mg/ml methanol). Varying concentrations (10 μl, 25 μl, and 100 μl) of glucose-6-phosphate dedydrogenase solutions were then added to the above solutions to form Solutions A, B and C, respectively. A control solution did not contain any enzyme. The fluorescence was then measured at 25° C.

The change in relative fluorescence per minute is shown in the Figure and indicates that RIND I can be used in a rapid assay for glucose-6-phosphate dehydrogenase.

EXAMPLE 9

Solution Assay for Nicotinamide Adenine Dinucleotide, Reduced Form and Ascorbate Using RIND I This example demonstrates the use of RIND I to assay for the biolotical reductants nicotinamide adenine dinucleotide, reduced form (NADH), and ascorbic acid.

Stock solutions of the following reagents were used: NADH (7.09 mg) in 10 ml distilled water, and Sodium ascorbate (1.98 mg) in 10 ml distilled water.

A dispersion of RIND I was prepared as described in Example 8, except that 0.05 molar potassium phosphate buffer was used.

Test solutions were prepared from the following components: 1.5 ml RIND I dispersion, 1.5 ml of 0.05 molar potassium phosphate buffer (pH 7.5) and 25 μl phenazine methosulfate solution (3 mg/ml methanol). Varying concentrations of the reductants, as shown in the tables, were added to these solutions. The fluorescence was then measured at 25° C. after 5 minutes for each reductant series, which included a control where reductant was absent. The results, listed in Tables III and IV below, indicate that RIND-I is useful in determinations of NADH and ascorbate, respectively.

TABLE III

Assay for NADH

| NADH Concentration | Relative Fluorescence (5 Min.) |
|---|---|
| Control | 0.042 |
| $3.3 \times 10^{-8}$ molar | 0.046 |
| $3.3 \times 10^{-7}$ molar | 0.043 |
| $3.3 \times 10^{-6}$ molar | 0.096 |
| $3.3 \times 10^{-5}$ molar | 0.370 |

TABLE IV

Assay for Ascorbic Acid

| NADH Concentration | Relative Fluorescence (5 Min.) |
|---|---|
| Control | 0.044 |
| $3.3 \times 10^{-8}$ molar | 0.049 |
| $3.3 \times 10^{-7}$ molar | 0.049 |
| $3.3 \times 10^{-6}$ molar | 0.096 |
| $3.3 \times 10^{-5}$ molar | 0.450 |

EXAMPLE 10

Solution Determination of *E. coli* Using RIND II and Several ETAs

The following stock solutions were used: electron transfer agents (ETA) in methanol (0.01 molar) and the *E. coli* concentration was $3 \times 10^7$ cells/ml.

Solutions were prepared from the following components; 1.5 ml RIND II dispersion, 1.5 ml potassium phosphate buffer, 25 μl glucose solution (10%), and 25 μl, of *E. coli* cells. Twenty-five microliters of the appropriate ETA were then added. A control solution did not contain any ETA. Fluorescence was then measured at initial time and 5, 15, and 30 minutes later.

The results, listed in Table V, indicate that RIND II is suitable in a 30-minute assay for *E. coli* using various ETAs.

TABLE V

| Solution | Relative Fluorescence | | | |
|---|---|---|---|---|
| | Initial Time | 5 Min | 15 Min | 30 Min |
| Control | 0.039 | 0.045 | 0.040 | 0.045 |
| PMS* | 0.022 | 0.042 | 0.11 | 0.28 |
| TMBQ** | 0.023 | 0.038 | 0.090 | 0.26 |
| DMHBQ*** | 0.024 | 0.039 | 0.096 | 0.26 |

*Phenazine methosulfate
**2,3,5-Trimethyl-1,4-benzoquinone
***2,3-Dimethyl-5-hydroxymethyl-1,4-benzoquinone

EXAMPLE 11

Detection of *E. coli* with RIND I in a Dry Element

A dry element having the following format was used in this example.

| | | |
|---|---|---|
| Spreading/ Reagent Layer | Poly(vinyltoluene-co-p-t-butylstyrene-co-methacrylic acid) Beads | 100–150 g/m² |
| | Poly(n-butyl acrylate-co-styrene-co-2-acrylamido-2-methylpropane sulfonic acid, sodium salt) | 2–6 g/m² |
| | TRITON X-100 surfactant | 2–5 g/m² |
| | Glucose | 0.1–0.5 g/m² |
| | RIND I | 0.1–0.5 g/m² |
| | 2,3,5-Trimethyl-1,4-benzoquinone | 0.8–4 g/m² |
| Reflection Layer | Gelatin (hardened) | 1–10 g/m² |
| | Titanium dioxide | 0.5–5.0 g/m² |
| | ZONYL FSN surfactant | 0.1–0.5 g/m² |
| | DAXAD 30 surfactant | 0.02–0.04 g/m² |
| Mordant/ Registration Layer | Gelatin (hardened) | 1–10 g/m² |
| | Poly(styrene-co-N—vinyl-benzyl-N,N—dimethyl-benzylammonium chloride-co-divinylbenzene) mordant | 0.05–5.0 g/m² |
| | ZONYL FSN surfactant | 0.1–0.5 g/m² |
| | Poly(ethylene terephthalate) Support | |

To evaluate this element, solutions of varying *E. coli* cell concentrations in potassium phosphate buffer (pH 7.5) and a Control containing only buffer were prepared. These solutions were then spotted onto the element using 10 μl drops, and the element was incubated at 37° C. for up to 60 minutes. The fluorescence was measured in a modified, conventional fluorometer (excitation, 540 nm, emission, 620 nm) after 3 minutes and at 60 minutes in the incubation period. The results, listed in Table VI below, show the difference (Δ) in relative fluorescence at 3 and 60 minutes, and they indicate that approximately $10^7$ cells/ml can be detected using this element.

TABLE VI

| *E. coli* (Cells/ml) | Δ Relative Fluorescence (57 Min., 37° C.) | Standard Deviation | CV (%)* |
|---|---|---|---|
| $1.0 \times 10^7$ | 0.272 | 0.007 | 2.6 |
| $4.1 \times 10^6$ | 0.249 | 0.007 | 2.8 |
| 0 | 0.221 | 0.010 | 4.5 |

*CV = Coefficient of Variation

EXAMPLE 12

Stability of the Fluorescent Dyes

A test solution was prepared from 25 μl of *E. coli* cells (approx. $1 \times 10^8$ cells/ml) in 0.05 molar potassium phosphate buffer, 25 μl glucose solution, 25 μl phenazine methosulfate (3 mg/ml methanol) and 25 μl of dye Compound I in methanol. When the optical density ws measured over 20 minutes at 545 nm in a commercially available Perkin-Elmer spectrophotometer, no density change was seen. This test shows that Dye I is stable, i.e. is not reduced in the presence of *E. coli* cells, an electron transfer agent and glucose.

In a similar test, the dye released from Control RIND D (see Example 13 below) was completely reduced in less than 4 minutes in the presence of *E. coli* cells (dispersion of TRITON X-100 surfactant and potassium phosphate buffer), phenazine methosulfate and glucose. The optical density was read at 650 nm.

EXAMPLE 13

Comparison of Stability of RIND Compounds Containing Different Fluorescent Dye Moieties This example compares the photolytic stability of a RIND compound useful in the present invention (RIND I) and Control RIND compounds containing fluorescent moieties outside the scope of this invention, some of which are commonly used in biological assays, i.e. 4-methylumbelliferone and fluorescein. Control RIND A is RIND XXIII compound from U.S. Ser. No. 824,766 of Belly et al noted above, containing a 4-methylumbelliferone moiety. Controls RIND B and RIND C contain a fluorescein moiety. Control RIND D contains a fluorescent acridine dye moiety.

Dispersions of each RIND compound were prepared by dissolving the RIND compound (4 μg) in N,N-dimethylformamide (250 μl), adding TRITON X-100 surfactant (0.5 μl), and slowly adding this mixture, with stirring, to 25 μl of 0.05 molar potassium phosphate (pH 7.5). These dispersion preparations were done under yellow lights. No reductants were added to these compositions.

Each dispersion (1.5 μl) and buffer (1.5 μl) were then placed in a quartz cell, and the fluorescence was determined at 25° C. in a Perkin-Elmer fluorescence spectrophotometer by exciting at the excitation maxima and detecting at the emission maxima of the respective released dyes. Ideally, no fluorescence should be detected at these wavelengths because a reductant is not present.

The results (Table VII) are expressed as the difference in the reading at initial time and after 15 minutes (Δ relative fluorescence). Control RIND B was read after one minute because of its high instability. Only RIND-I of this invention and Control RIND D were stable under these conditions. However, the released dye from Control RIND D is rapidly reduced in the presence of living cells, ETA and glucose. The released dye from RIND I is not reduced under similar conditions. Therefore, only RIND I and its released dye are both stable in biological conditions generally used for analytical determinations.

TABLE VII

Stability Comparison of RIND Compounds

| Compound | Excitation λ (nm) Dye | Emission λ (nm) Dye | Δ Relative Fluorescence (15 Min) |
|---|---|---|---|
| RIND-I | 540 | 620 | 0.1 |
| RIND-A | 370 | 450 | 240 |
| RIND-B | 495 | 520 | 865* |
| RIND-C | 495 | 520 | 10.8 |
| RIND-D | 600 | 666 | 0.1 |

*Reading after one minute.

The invention has been described in detail with particular reference to preferred embodiments thereof, but it will be understood that variations and modifications can be effected within the spirit and scope of the invention.

We claim:

1. An analytical test composition buffered to a pH of 9 or less, said composition comprising a fluorescent dye selected from the group consisting of

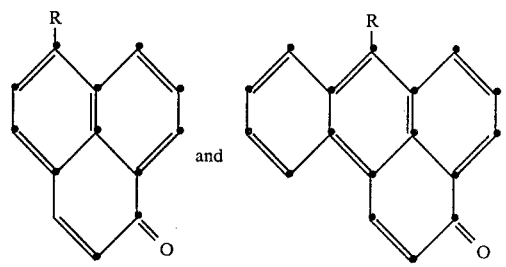

wherein R is hydroxy, mercapto or amino or salts thereof.

2. The composition of claim 1 wherein amino is HN(R')— and wherein R' is hydrogen, alkyl, phenyl, cyclohexyl or a heterocyclic group.

3. The composition of claim 1 hwerein said fluorescent dye is

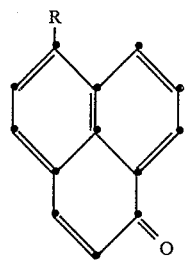

wherein R is hydroxy or amino or salts thereof.

4. An analytical composition comprising a reducible compound of the structure CAR—(R¹)ₙ wherein CAR— is an aromatic or quinone nucleus having a hydrogen atom removed to provide a valence through which R¹ is attached to CAR—, R¹ comprises a fluorescent moiety derived from a compound selected from the group consisting of

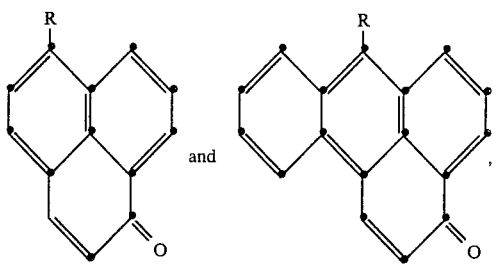  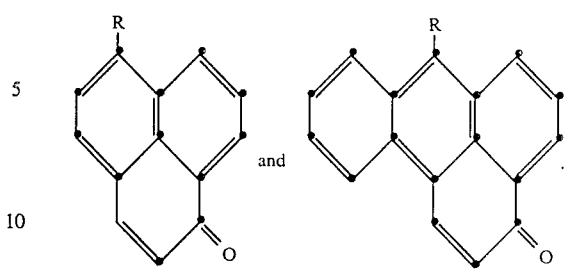

wherein
- R is hydroxy or mercapto or salts thereof, and n is 1 or 2, said fluorescent moiety having an oxy or thio linkage, derived from said R group by removal of a hydrogen atom, through which said moiety is attached to said CAR— nucleus,
- provided CAR-(-R$^1$)$_n$ is constructed so that it is capable of being reduced at a pH of 9 or less to release said derived fluorescent moiety, and
- further provided that when R$^1$ is replaced with H, CAR-(-H)$_n$ has an E$_{\frac{1}{2}}$ of at least about +100 mV when measured in water.

5. The composition of claim 4 wherein said reducible compound has the structure

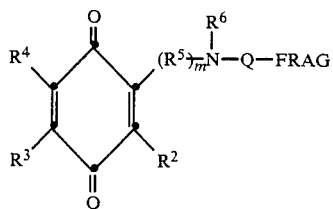

wherein
- R$^2$ and R$^4$ are independently hydrogen, alkyl, aryl or an electron withdrawing group having a positive Hammett sigma value,
- R$^3$ is R$^1$, hydrogen, alkyl, aryl or an electron withdrawing group having a positive Hammett sigma value, or R$^3$ and R$^4$, taken together, represent the atoms necessary to complete a fused carbocyclic ring,
- R$^5$ is alkylene of 1 or 2 carbon atoms,
- R$^6$ is methy,
- Q is carbonyl or thiocarbonyl,
- FRAG is said fluorescent moiety attached to Q through said oxy or thio linkage, and
- m is 0 or 1.

6. The composition of claim 4 further comprising a surfactant.

7. The composition of claim 4 further comprising an electron transfer agent.

8. A dry analytical element for the determination of an analyte comprising an absorbent carrier material, and containing a reducible compound of the structure CA-R-(-R$^1$)$_n$ wherein CAR— is an aromatic or quinone nucleus having a hydrogen atom removed to provide a valence through which R$^1$ is attached to CAR—, R$^1$ comprises a fluorescent moiety derived from a compound selected from the group consisting of wherein
- R is hydroxyl or mercapto or salts thereof, and n is 1 or 2, said fluorescent moiety having an oxy or thio linkage, derived from said R group by removal of a hydrogen atom, through which said moiety is attached to said CAR— nucleus,
- provided CAR-(-R$^1$)$_n$ is constructed so that it is capable of being reduced at a pH of 9 or less to release said derived fluorescent moiety, and
- further provided that when R$^1$ is replaced with H, CAR-(-H)$_n$ has an E$_{\frac{1}{2}}$ of at least about +100 mV when measured in water.

9. The element of claim 8 further containing an electron transfer agent.

10. The element of claim 8 wherein said reducible compound has the structure

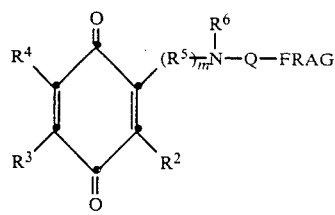

wherein
- R$^2$ and R$^4$ are independently hydrogen, alkyl, aryl or an electron withdrawing group having a positive Hammett sigma value,
- R$^3$ is R$^1$, hydrogen, alkyl, aryl or an electron withdrawing group having a positive Hammett sigma value, or R$^3$ and R$^4$, taken together, represent the atoms necessary to complete a fused carbocyclic ring,
- R$^5$ is alkylene of 1 or 2 carbon atoms,
- R$^6$ is methyl,
- Q is carbonyl or thiocarbonyl,
- FRAG is said fluorescent moiety attached to Q through said oxy or thio linkage, and
- m is 0 or 1.

11. The element of claim 10 wherein R$^3$ is R$^1$.

12. The element of claim 10 wherein R$^5$ is methylene, R$^6$ is methyl and Q is carbonyl.

13. The element of claim 10 comprising a support carrying said absorbent carrier material.

14. A dry analytical element for making a determination of living organisms comprising a support having thereon a porous spreading zone, and containing an electron transfer agent and a reducible compound of the structure

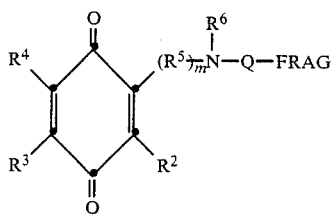

wherein
- $R^2$ and $R^4$ are independently hydrogen, alkyl, aryl or an electron withdrawing group having a positive Hammett sigma value,
- $R^3$ is $R^1$, hydrogen, alkyl, aryl or an electron withdrawing group having a positive Hammett sigma value, or $R^3$ and $R^4$, taken together, represent the atoms necessary to complete a fused carbocyclic ring,
- $R^5$ is alkylene of 1 or 2 carbon atoms,
- $R^6$ is methyl,
- Q is carbonyl or thiocarbonyl,
- FRAG is a fluorescent moiety derived from a compound selected from the group consisting of

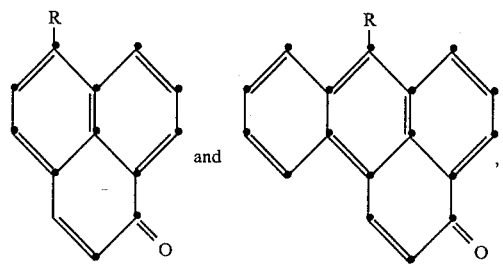

wherein R is hydroxy or mercapto or salts thereof, and m is 0 or 1, said fluorescent moiety having an oxy or thio linkage, derived from said R group by removal of a hydrogen atom, through which said moiety is attached to said CAR— nucleus, provided that when $R^1$ is replaced with H, CAR—H has an $E_{\frac{1}{2}}$ of at least about +100 mV when measured in water.

15. The element of claim 14 further comprising a carbon source nutrient for living organisms.

16. A method for the determination of an analyte comprising the steps of:

A. at a pH of 9 or less, contacting a sample of a liquid suspected of containing analyte with a reducible compound of the structure CAR-(-$R^1$)$_n$ wherein CAR— is an aromatic or quinone nucleus having a hydrogen atom removed to provide a valence through which $R^1$ is attached to CAR—, $R^1$ comprises a fluorescent moiety derived from a compound selected from the group consisting of

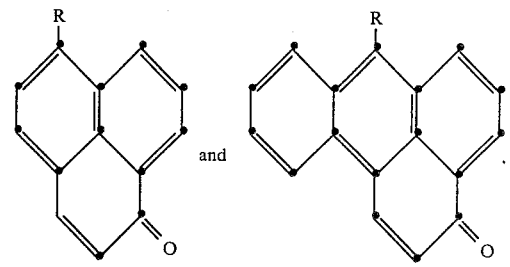

wherein
- R is hydroxyl or mercapto or salts thereof, and n is 1 or 2, said fluorescent moiety having an oxy or thio linkage, derived from said R group by removal of a hydrogen atom, through which said moiety is attached to said CAR— nucleus,
- provided CAR-(-$R^1$)$_n$ is constructed so that it is capable of being reduced at said pH to release said derived fluorescent moiety; and
- further provided that when $R^1$ is replaced with H, CAR-(-H)$_n$ has an $E_{\frac{1}{2}}$ of at least about +100 mV when measured in water, and B. detecting said derived fluorescent moiety released from said compound upon its reduction as a result of the presence of said analyte.

17. The method of claim 16 wherein said reducible compound has the structure

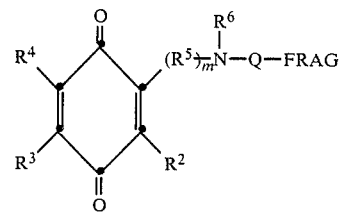

wherein
- $R^2$ and $R^4$ are independently hydrogen, alkyl, aryl or an electron withdrawing group having a positive Hammett sigma value,
- $R^3$ is $R^1$, hydrogen, alkyl, aryl or an electron withdrawing group having a positive Hammett sigma value, or $R^3$ and $R^4$, taken together, represent the atoms necessary to complete a fused carbocyclic ring,
- $R^5$ is alkylene of 1 or 2 carbon atoms,
- $R^6$ is methyl,
- Q is carbonyl or thiocarbonyl,
- FRAG is said fluorescent moiety attached to Q through said oxy or thio linkage, and
- m is 0 or 1.

18. The method of claim 16 for the determination of a living organism in the presence of an electron transfer agent.

19. The method of claim 16 wherein when said compound is reduced at about pH 7, at least about 50% of said fluorescent moiety is released within about 30 minutes.

20. The method of claim 16 wherein said fluorescent moiety is derived from

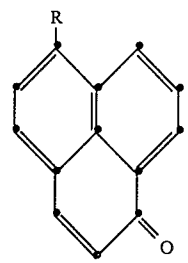

wherein R is hydroxy or amino or salts thereof.

21. A method for staining a biological specimen comprising contacting a biological specimen with a composition buffered to a pH of 9 or less, which composition comprises a fluorescent compound selected from the group consisting of

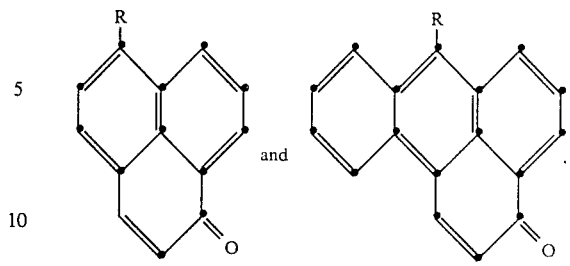

wherein R is hydroxy, mercapto or amino or salts thereof.

22. A compound of the structure

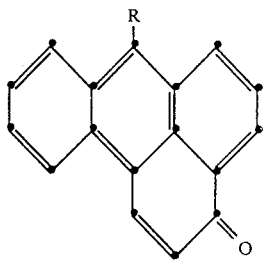

wherein R is hydroxy, mercapto or amino or salts thereof.

* * * * *